US012779160B2

(12) United States Patent
Takehara et al.

(10) Patent No.: US 12,779,160 B2
(45) Date of Patent: Nov. 3, 2026

(54) CPAP DEVICE AND POWER CONTROL PROGRAM FOR THE SAME

(71) Applicant: Murata Manufacturing Co., Ltd., Kyoto (JP)

(72) Inventors: Yu Takehara, Kyoto (JP); Masayuki Shirai, Kyoto (JP); Masayuki Shirai, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 414 days.

(21) Appl. No.: 18/589,699

(22) Filed: Feb. 28, 2024

(65) Prior Publication Data

US 2024/0307640 A1 Sep. 19, 2024

(30) Foreign Application Priority Data

Mar. 17, 2023 (JP) ................................ 2023-043155

(51) Int. Cl.
*A61M 16/00* (2006.01)
*A61M 16/06* (2006.01)
(Continued)

(52) U.S. Cl.
CPC ...... *A61M 16/024* (2017.08); *A61M 16/0003* (2014.02); *A61M 16/0066* (2013.01); *A61M 16/06* (2013.01); *A61M 16/0875* (2013.01); *A61M 16/1085* (2014.02); *A61M 16/109* (2014.02); *A61M 2016/0033* (2013.01); *A61M 2202/0007* (2013.01); *A61M 2202/02* (2013.01); *A61M 2205/10* (2013.01);
(Continued)

(58) Field of Classification Search
CPC .............. A61M 16/024; A61M 16/026; A61M 16/0003; A61M 16/0066; A61M 16/06; A61M 16/0875; A61M 16/1085; A61M 16/1095; A61M 16/16; A61M 16/0069; A61M 2016/0033; A61M 2205/14
See application file for complete search history.

(56) References Cited

U.S. PATENT DOCUMENTS

2010/0065054 A1* 3/2010 Bowman ........... A61M 16/0051 128/204.21
2011/0162647 A1* 7/2011 Huby ................ A61M 16/0003 128/203.14
(Continued)

FOREIGN PATENT DOCUMENTS

JP 2022-505058 A 1/2022

*Primary Examiner* — Douglas Y Sul
(74) *Attorney, Agent, or Firm* — McDonald Hopkins LLC

(57) ABSTRACT

A CPAP device includes a blower, a tube heater, a humidifier, and a controller that controls power supply to these components. The controller calculates each of first supply power to the blower, second supply power to the tube heater, and third supply power to the humidifier. The controller provides the first supply power to the blower and the second supply power to the tube heater. In contrast, the controller provides, to the humidifier, lower one of the third supply power and remainder power obtained by subtracting the first supply power and the second supply power from the predetermined upper limit. If the sum total of the first supply power to the third supply power exceeds the upper limit, the controller decreases the second supply power until the sum total decreases to or below the upper limit.

6 Claims, 5 Drawing Sheets

(51) Int. Cl.
*A61M 16/08* (2006.01)
*A61M 16/10* (2006.01)

(52) U.S. Cl.
CPC . *A61M 2205/14* (2013.01); *A61M 2205/3327* (2013.01); *A61M 2205/3334* (2013.01); *A61M 2205/3368* (2013.01); *A61M 2205/3653* (2013.01); *A61M 2205/42* (2013.01); *A61M 2205/50* (2013.01); *A61M 2210/0618* (2013.01); *A61M 2210/0625* (2013.01)

(56) References Cited

U.S. PATENT DOCUMENTS

| | | | | |
|---|---|---|---|---|
| 2016/0213869 | A1* | 7/2016 | Feldhahn .......... | A61M 16/0051 |
| 2020/0114098 | A1* | 4/2020 | Bath ................. | A61M 16/0066 |
| 2021/0008312 | A1* | 1/2021 | Young ................. | A61M 16/021 |
| 2022/0184330 | A1* | 6/2022 | Zhan ................... | A61M 16/024 |
| 2022/0249798 | A1* | 8/2022 | Doudkine ........... | A61M 16/024 |

* cited by examiner

CPAP DEVICE AND POWER CONTROL PROGRAM FOR THE SAME

CROSS REFERENCE TO RELATED APPLICATION

This application claims priority from Japanese Patent Application No. 2023-043155 filed on Mar. 17, 2023. The content of this application is incorporated herein by reference in its entirety.

BACKGROUND OF THE DISCLOSURE

1. Field of the Disclosure

The present disclosure relates to a continuous positive airway pressure (CPAP) device and a power control program for the CPAP device.

2. Description of the Related Art

A CPAP device disclosed in Japanese Unexamined Patent Application Publication (Translation of PCT) No. 2022-505058 includes a blower and an air path through which air blown by the blower flows. A mask is attached to the downstream end of the air path. A user uses the CPAP device with the mask covering the nose and the mouth. The CPAP device disclosed in Japanese Unexamined Patent Application Publication (Translation of PCT) No. 2022-505058 also includes a humidifier for humidifying the air in the air path. Further, in the CPAP device, part of the air path forms a heating pipe for heating the air.

The CPAP device disclosed in Japanese Unexamined Patent Application Publication (Translation of PCT) No. 2022-505058 includes a controller that controls supply power to the blower, the humidifier, and the heating pipe. The controller calculates a mean value of the overall power consumption in a given cycle. If the overall mean value of the calculated power consumption exceeds a rated power, the controller decreases supply power to the humidifier and the heating pipe.

BRIEF SUMMARY OF THE DISCLOSURE

Japanese Unexamined Patent Application Publication (Translation of PCT) No. 2022-505058 does not specifically disclose how and which one of the supply power to the humidifier and the supply power to the heating pipe is decreased in decreasing the supply power to the humidifier and the heating pipe. There is thus still room for improvement in a viewpoint of appropriately controlling the power supply and minimizing the user's feel impairment.

A CPAP device that addresses the issue above includes: a blower that blows air; a tube that allows air blown by the blower to flow through the tube; a tube heater that heats the air in the tube; a humidifier that humidifies the air blown into the tube; and a controller that controls power supply to the blower, the humidifier, and the tube heater. In the CPAP device, the controller is configured to execute a supply power calculation process, a determination process, a power supply process, and a changing process. In the supply power calculation process, each of first supply power to the blower, second supply power to the tube heater, and third supply power to the humidifier is calculated. In the determination process, whether a sum total of the first supply power, the second supply power, and the third supply power exceeds a predetermined upper limit is determined. In the power supply process, the first supply power is supplied to the blower, the second supply power is supplied to the tube heater, and lower one of remainder power and the third supply power is supplied to the humidifier, the remainder power being obtained by subtracting the first supply power and the second supply power from the upper limit. In the changing process, in response to the sum total exceeding the upper limit, the second supply power is decreased until the sum total decreases to or below the upper limit.

A power control program for a CPAP device addresses the issue above, the CPAP device including a blower that blows air, a tube that allows air blown by the blower to flow through the tube, a tube heater that heats the air in the tube, a humidifier that humidifies the air blown into the tube, and a controller that controls power supply to the blower, the humidifier, and the tube heater. The program causes the controller to execute a supply power calculation process, a determination process, a power supply process, and a changing process. In the supply power calculation process, each of first supply power to the blower, second supply power to the tube heater, and third supply power to the humidifier is calculated. In the determination process, whether a sum total of the first supply power, the second supply power, and the third supply power exceeds a predetermined upper limit is determined. In the power supply process, the first supply power is supplied to the blower, the second supply power is supplied to the tube heater, and lower one of remainder power and the third supply power is supplied to the humidifier, the remainder power being obtained by subtracting the first supply power and the second supply power from the upper limit. In the changing process, in response to the sum total exceeding the upper limit, the second supply power is decreased until the sum total decreases to or below the upper limit.

According to the configuration above, even if the sum total of the first to third supply power to the air exceeds the upper limit from the state where the sum total is lower than or equal to the upper limit, the temperature and the humidity of the air to be supplied to the user may be prevented from decreasing. Accordingly, it is less likely to impair the user's feel.

DETAILED DESCRIPTION OF THE DISCLOSURE

Hereinafter, an embodiment of a CPAP device will be described. The drawings illustrate enlarged components on occasions for easy understanding. The ratio of the dimensions of the components are different from an actual ratio or a ratio in a different drawing on occasions.

CPAP Device Structure

Figure 1:
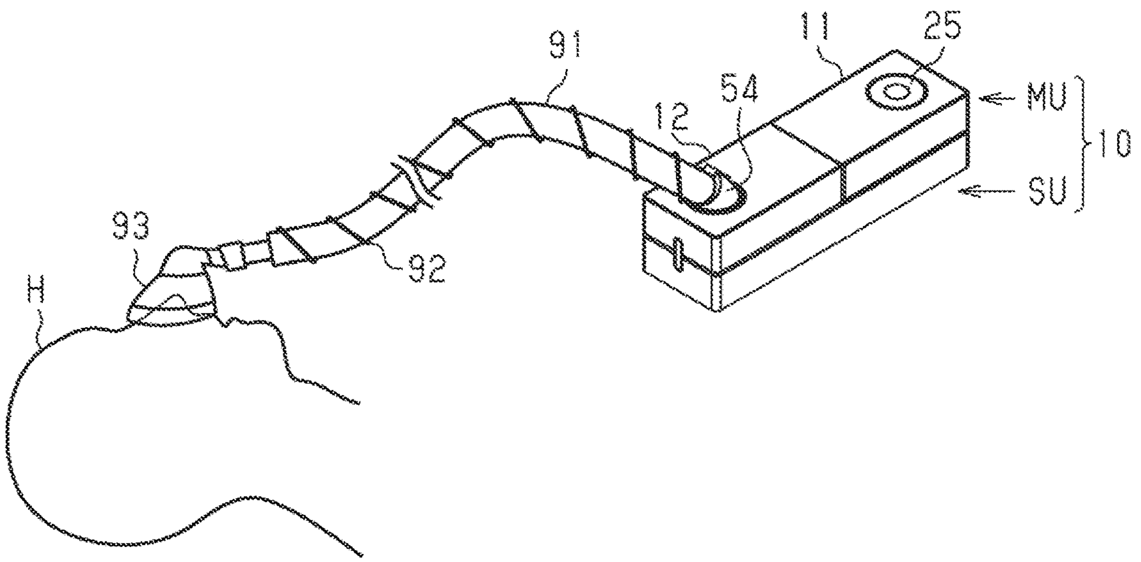
FIG. 1 is a view illustrating a state where a CPAP device is used (in-use state) in a docking state.

First, a CPAP device 10 will be described. As illustrated in FIG. 1, the CPAP device 10 includes a main unit MU and a sub unit SU. In a state where the sub unit SU is attached to the main unit MU, the CPAP device 10 is in the shape of a substantially rectangular parallelepiped as a whole. The state where the sub unit SU is attached to the main unit MU is hereinafter referred to as a docking state on occasions.

Figure 2:
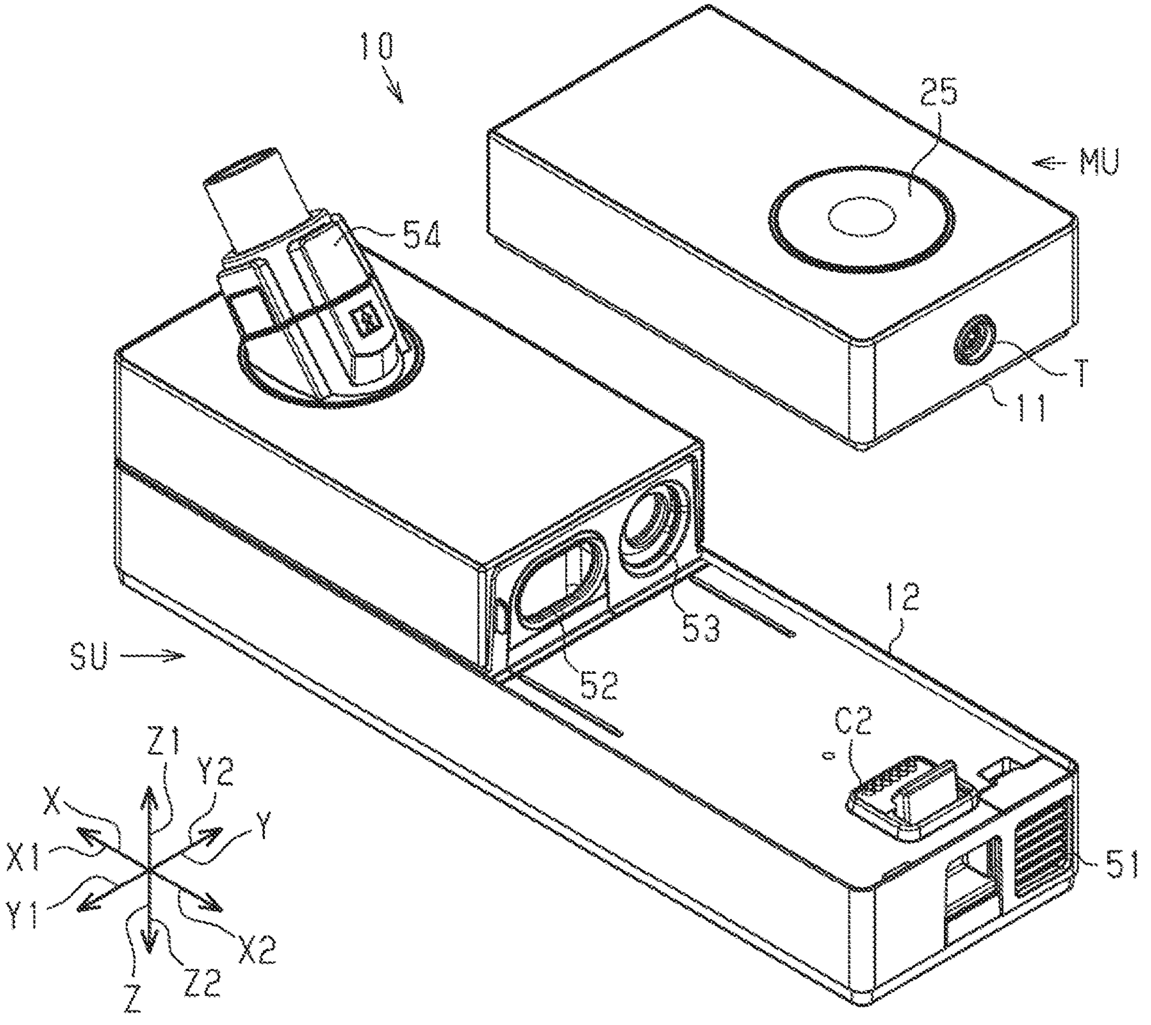
FIG. 2 is a perspective view of the CPAP device.
Figure 4:
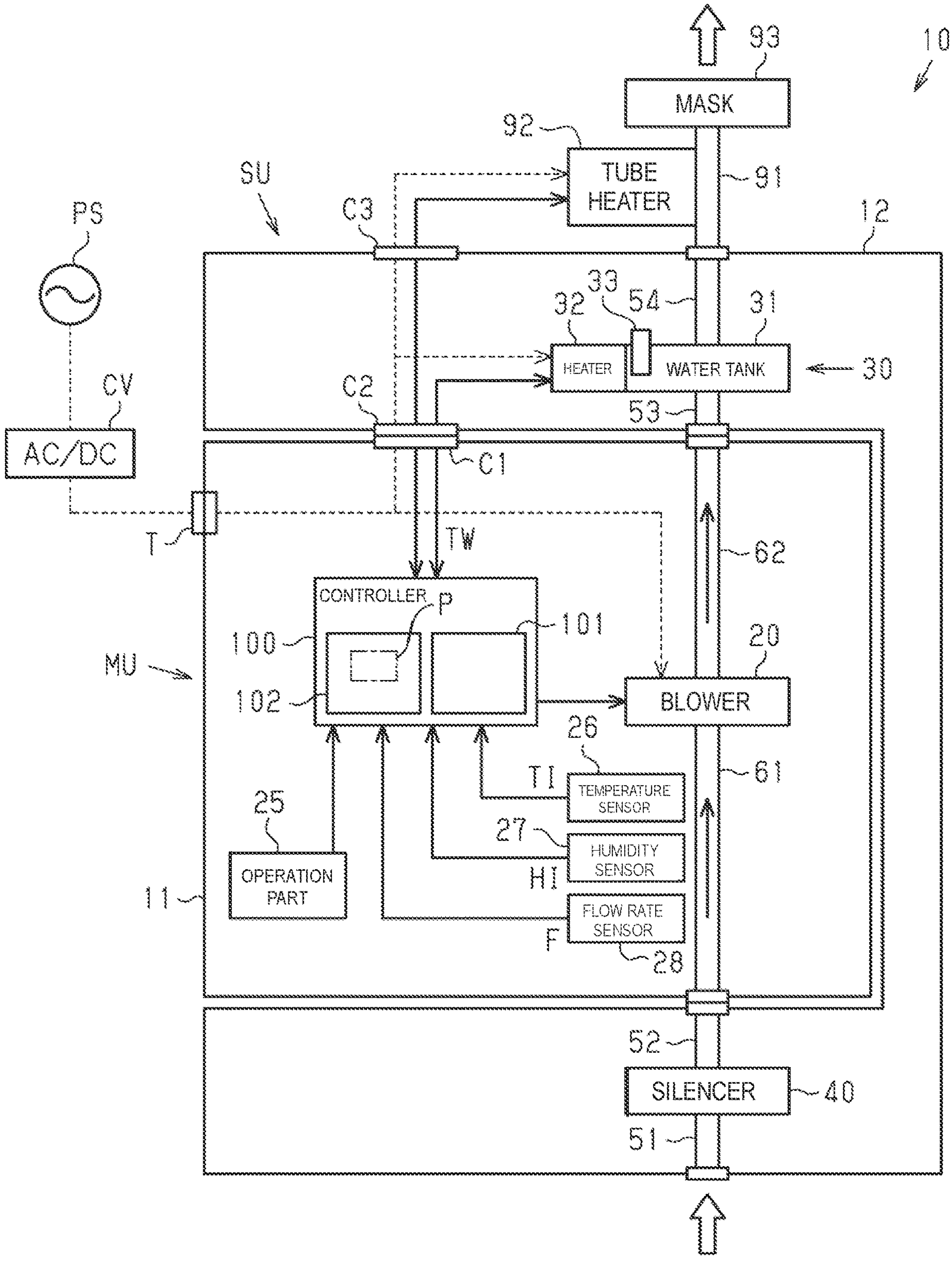
FIG. 4 is a schematic configuration view of the CPAP device.

As illustrated in FIG. 2, the main unit MU includes a first enclosure 11. The first enclosure 11 is a substantially rectangular parallelepiped having a hollow portion therein. As illustrated in FIG. 4, the main unit MU includes a blower 20 that blows air. The blower 20 is contained in the first enclosure 11. Although the illustration of the blower is omitted, the blower 20 has an electric motor, an air blow fan rotated by the electric motor, and the like. Specifically, the blower 20 is an electrical component.

The main unit MU includes an upstream passage 61 and a downstream passage 62. The upstream passage 61 and the downstream passage 62 are defined in the first enclosure 11. The upstream end of the upstream passage 61 is open to the outside of the first enclosure 11. The downstream end of the upstream passage 61 is connected to the blower 20 on the upstream side of the blower 20. The upstream end of the downstream passage 62 is connected to the blower 20 on the downstream side of the blower 20. The downstream end of the downstream passage 62 is open to the outside of the first enclosure 11. The blower 20 thus sucks up air in the upstream passage 61 and blows the air into the downstream passage 62.

As illustrated in FIG. 2, the main unit MU includes an operation part 25. The operation part 25 is exposed from the upper surface of the first enclosure 11. The operation part 25 is a physical push button for operations such as turning on and off the CPAP device 10.

The sub unit SU of the CPAP device 10 includes a second enclosure 12. The second enclosure 12 is in an L-shape in a side view in a width direction. By fitting the first enclosure 11 in the inside of the L-shape of the second enclosure 12, the CPAP device 10 forms the substantially rectangular parallelepiped as described above. The second enclosure 12 of the sub unit SU is thus attachable to and detachable from the first enclosure 11 of the main unit MU.

As illustrated in FIG. 4, the sub unit SU has a humidifier 30 and a silencer 40. The silencer 40 is provided to silence a noise generated in response to driving the blower 20. The silencer 40 is defined in the second enclosure 12. Although the illustration of the silencer 40 is omitted, the silencer 40 has a flow passage for the air and a silencer chamber to which the variation in the pressure of the air in the flow passage is transmittable.

The humidifier 30 has a water tank 31 capable of storing water therein, a heater 32 that heats the water in the water tank 31, and a water temperature sensor 33 that detects water temperature TW in the water tank 31. The air blown from the blower 20 may flow into the water tank 31. The heater 32 has a heater resistor (not illustrated). The heater 32 generates heat in response to current flowing through the heater resistor. The heat is transmitted to the water tank 31 with a heater plate (not illustrated) interposed between the heater 32 and the water tank 31, and thereby the water in the water tank 31 is heated. Warming up the water in the water tank 31 causes the water to volatilize easily, and thus the air blown by the blower 20 is heated. As described above, the humidifier 30 is an electrical component.

The sub unit SU has a first passage 51, a second passage 52, a third passage 53, and a fourth passage 54. The first passage 51 is defined in the second enclosure 12. The upstream end of the first passage 51 is open to the outside of the second enclosure 12. The downstream end of the first passage 51 is connected to the silencer 40. The second passage 52 is defined in the second enclosure 12. The upstream end of the second passage 52 is connected to the silencer 40. The downstream end of the second passage 52 is open to the outside of the second enclosure 12.

The third passage 53 is defined in the second enclosure 12. The upstream end of the third passage 53 is open to the outside of the second enclosure 12. The downstream end of the third passage 53 is connected to the water tank 31 of the humidifier 30. The fourth passage 54 is defined in the second enclosure 12. The upstream end of the fourth passage 54 is connected to the water tank 31. The downstream end of the fourth passage 54 is open to the outside of the second enclosure 12.

Figure 3:
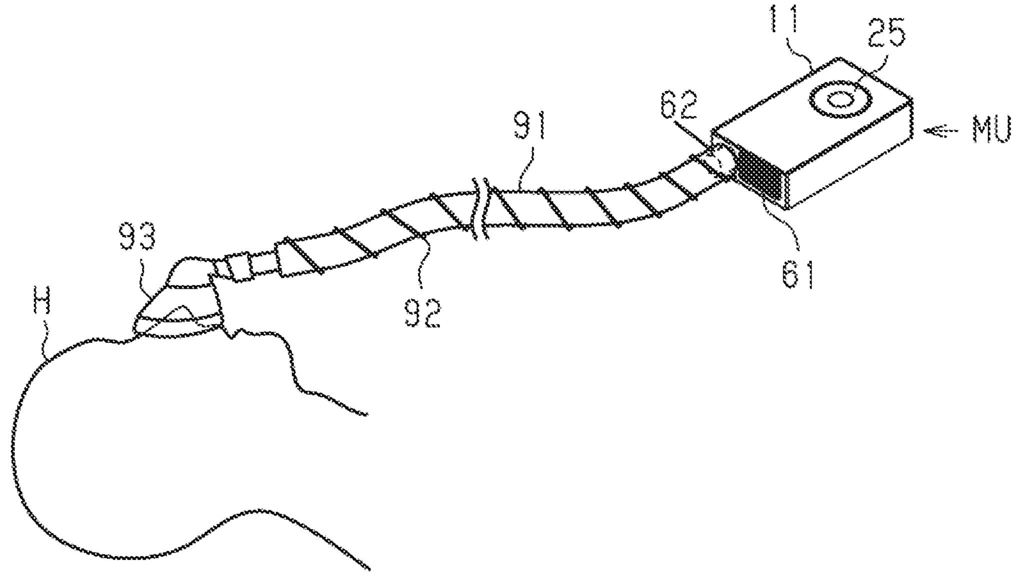
FIG. 3 is a view illustrating the in-use state of the CPAP device with a main unit used alone.

As illustrated in FIG. 1, the CPAP device 10 includes a tube 91, a tube heater 92, and a mask 93. The tube 91 is a tubular component that allows the air blown by the blower 20 to flow therethrough. The upstream end of the tube 91 is attachable to and detachable from the downstream end of the fourth passage 54 of the sub unit SU. As illustrated in FIG. 3, the upstream end of the tube 91 is also attachable to and detachable from the downstream end of the downstream passage 62 of the main unit MU.

As illustrated in FIG. 1, the tube heater 92 is in a substantially band shape. The tube heater 92 is helically wound around the circumferential surface of the tube 91. Although the illustration of the tube heater 92 is omitted, the tube heater 92 has a filamentous heating wire and a synthetic resin covering the heating wire. In response to the current flowing through the heating wire of the tube heater 92, the tube heater 92 generates heat, and thus the air in the tube 91 is heated. The mask 93 is attachable to and detachable from the downstream end of the tube 91. In using the CPAP device 10, the mask 93 is worn by a user H in such a manner as to cover the nose or the mouth of the user H.

Air Flowing Path of CPAP Device in In-Use State

As described above, the second enclosure 12 of the sub unit SU is attachable to the first enclosure 11 of the main unit MU. In the docking state where the second enclosure 12 is attached to the first enclosure 11, the passages in the main unit MU and the passages of the sub unit SU become interconnected. Specifically, as illustrated in FIG. 4, in the docking state, the upstream end of the upstream passage 61 in the main unit MU is connected to the downstream end of the second passage 52 in the sub unit SU. The downstream end of the downstream passage 62 in the main unit MU is connected to the upstream end of the third passage 53 in the sub unit SU. Accordingly, in response to the blower 20 being driven in the docking state, the air taken from the first passage 51 reaches the blower 20 via the silencer 40, the second passage 52, and the upstream passage 61. The air blown by the blower 20 then reaches the mask 93 via the downstream passage 62, the third passage 53, the water tank 31 of the humidifier 30, the fourth passage 54, and the tube 91.

In contrast, as illustrated in FIG. 3, the CPAP device 10 is usable in a state where the sub unit SU is detached from the main unit MU. In response to the blower 20 being driven in a non-docking state, the air taken from the upstream passage 61 reaches the blower 20. The air blown by the blower 20 then reaches the mask 93 via the downstream passage 62 and the tube 91.

Electrical Configuration of CPAP Device

As illustrated in FIG. 4, the main unit MU includes a controller 100. The controller 100 includes a memory 102 and a computing unit 101. The computing unit 101 is capable of running various programs stored in the memory 102. The computing unit 101 is capable of writing data to the memory 102 in running a program. The memory 102 includes a read-only memory (ROM) that is only readable, a readable and writable volatile random-access memory (RAM), and a readable and writable nonvolatile storage. The memory 102 stores a power control program P for performing power control (described later).

The controller 100 acquires a signal from the operation part 25. Based on the signal acquired from the operation part 25, the controller 100 outputs a control signal to each of the blower 20, the heater 32 of the humidifier 30, and the tube heater 92. The controller 100 then controls power supply to each of the blower 20, the heater 32 of the humidifier 30, and the tube heater 92 by using the control signal.

The main unit MU includes a temperature sensor 26, a humidity sensor 27, and a flow rate sensor 28. The temperature sensor 26 detects the temperature of the air in the upstream passage 61 as inlet temperature TI. The temperature sensor 26 outputs a signal indicating the detected inlet temperature TI to the controller 100. The humidity sensor 27 detects the relative humidity of the air in the upstream passage 61 as inlet humidity HI. The humidity sensor 27 outputs a signal indicating the detected inlet humidity HI to the controller 100. The flow rate sensor 28 detects the flow rate per unit time of air flowing through the upstream passage 61 as an air flow rate F. The flow rate sensor 28 outputs a signal indicating the detected air flow rate F to the controller 100.

As illustrated in FIG. 4, the main unit MU includes a power input terminal T. The power input terminal T may connect a power supply cable from an external power supply to the main unit MU. The external power supply is, for example, an alternating-current/direct-current (AC/DC) converter CV that converts AC power from a commercial AC power supply PS to DC power. The blower 20 of the main unit MU receives power supply via the power input terminal T.

The main unit MU includes a first connector C1. The first connector C1 puts signal lines, power lines, and the like together. The main unit MU performs power supply to the sub unit SU by using the first connector C1. The main unit MU transmits and receives data to and from the sub unit SU with the first connector C1 interposed therebetween.

As illustrated in FIG. 2, the sub unit SU includes a second connector C2. The second connector C2 puts signal lines, power lines, and the like together. As illustrated in FIG. 4, when the CPAP device 10 is in the docking state, the second connector C2 is connected to the first connector C1. The heater 32 of the humidifier 30 receives power supply from the main unit MU via the second connector C2. The sub unit SU transmits and receives data to and from the main unit MU via the second connector C2. For example, the water temperature sensor 33 of the humidifier 30 in the sub unit SU outputs the detected water temperature TW to the controller 100 via the second connector C2 and the first connector C1.

The sub unit SU also includes a third connector C3. The third connector C3 puts signal lines, power lines, and the like together. The third connector C3 is connectable to the tube heater 92. The tube heater 92 receives power supply via the third connector C3 of the sub unit SU. If the CPAP device 10 is used with the main unit MU alone, it is not possible for the tube heater 92 to receive the power supply via the third connector C3. That is, the tube 91 itself is attachable to and detachable from the main unit MU, but the tube heater 92 functions only in the docking state.

Power Control by Controller

The computing unit 101 of the controller 100 is capable of performing power control for controlling the power supply to the blower 20, the heater 32 of the humidifier 30, and the tube heater 92 by running the power control program P stored in the memory 102. The power control is started when the CPAP device 10 starts therapy operation in response to the operation or the like of the operation part 25. The power control is terminated when the CPAP device 10 terminates the therapy operation in response to the operation or the like of the operation part 25.

Figure 5:
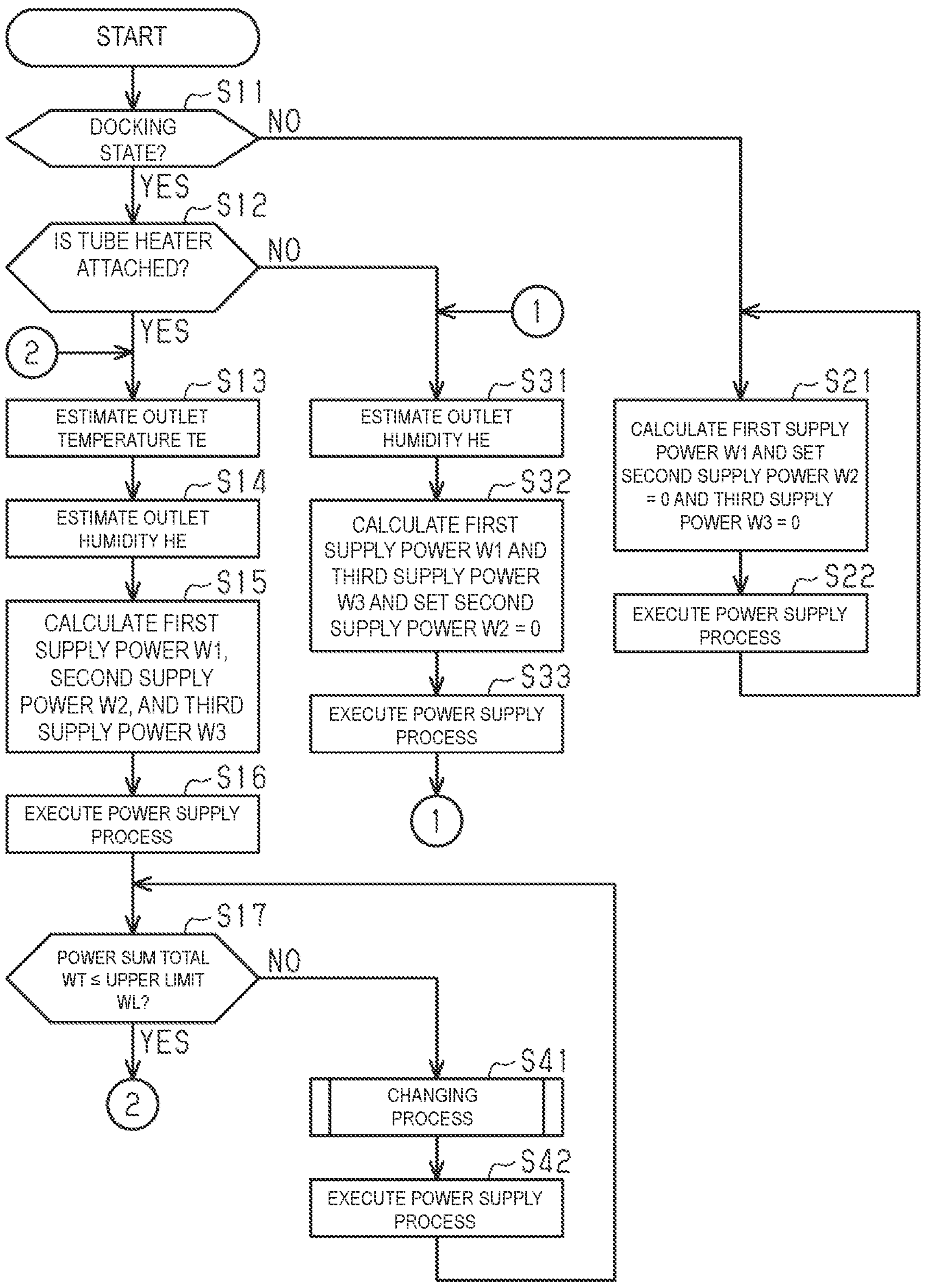
FIG. 5 is a flowchart of power control.

As illustrated in FIG. 5, after the power control is started, the controller 100 first performs step S11. In step S11, the controller 100 determines whether the CPAP device 10 is in the docking state. For example, based on whether the signal transmission and reception via the first connector C1 succeed, the potential of the power line of the first connector C1, or the like, the controller 100 determines whether the CPAP device 10 is in the docking state. If it is determined that the CPAP device 10 is not in the docking state in step S11 (NO in step S11), the process by the controller 100 moves to step S21.

In step S21, the controller 100 executes a supply power calculation process. The supply power calculation process is a process in which each of first supply power W1 to the blower 20, second supply power W2 to the tube heater 92, and third supply power W3 to the heater 32 of the humidifier 30 is calculated. In step S21 as the supply power calculation process, the controller 100 sets both of the second supply power W2 and the third supply power W3 to zero. The controller 100 calculates the first supply power W1 to the blower 20 to cause the air flow rate F detected by the flow rate sensor 28 to coincide with a target flow rate. For example, if the air flow rate F is lower than the target flow rate, the controller 100 makes the first supply power W1 higher than that in the current state. In contrast, if the air flow rate F exceeds the target flow rate, the controller 100 makes the first supply power W1 lower than that in the current state. At this time, the greater a difference between the air flow rate F and the target flow rate, the more the controller 100 increases a variation in first supply power W1 before and after the change. As described above, the controller 100 performs, on the first supply power W1, feedback control based on the difference between the air flow rate F and the target flow rate, for example, proportional integral (PI) control.

The target flow rate described above is specified in advance by a medical worker such as a doctor and is stored in the memory 102 of the controller 100. The target flow rate is changed one after another at the timing of exhaling and inhaling by the user H, or the like. After step S21, the process by the controller 100 moves to step S22.

In step S22, the controller 100 executes the power supply process. Specifically, the controller 100 supplies each supply power calculated in step S21 to a corresponding one of the blower 20, the tube heater 92, and the heater 32 of the humidifier 30 for a fixed period of time. In the case where the process in step S22 is executed, the second supply power W2 and the third supply power W3 are both zero as described above. The first supply power W1 is supplied to only the blower 20. Thereafter, the process by the controller 100 again moves to step S21. Specifically, the controller 100 repeats steps S21 and S22.

In contrast, if it is determined that the CPAP device is in the docking state in step S11 (YES in step S11), the process by the controller 100 moves to step S12.

In step S12, the controller 100 determines whether the tube heater 92 is properly attached. For example, based on whether the signal transmission and reception via the first connector C1 succeed, the potential of the power line of the first connector C1, or the like, the controller 100 determines whether the tube heater 92 is properly attached. If it is determined that the tube heater 92 is not attached (NO in step S12), the process by the controller 100 moves to step S31.

In step S31, the controller 100 estimates outlet humidity HE as the humidity of the air in the tube 91 and acquires the outlet humidity HE. Specifically, the controller 100 estimates the outlet humidity HE by adding an increase in humidity caused by the humidifier 30 to the inlet humidity HI detected by the humidity sensor 27. The higher the water temperature TW detected by the water temperature sensor 33, the larger the increase in humidity caused by the humidifier 30. In contrast, the higher the air flow rate F detected by the flow rate sensor 28, the smaller the increase in humidity caused by the humidifier 30. Thereafter, the process by the controller 100 moves to step S32.

In step S32, the controller 100 executes the supply power calculation process. In step S32 as the supply power calculation process, the controller 100 sets the second supply power W2 to zero. The controller 100 also calculates the first supply power W1 to the blower 20 to cause the air flow rate F detected by the flow rate sensor 28 to coincide with the target flow rate. The first supply power W1 is calculated in the same manner as in step S21.

Further, the controller 100 calculates the third supply power W3 to the heater 32 of the humidifier 30 to cause the outlet humidity HE estimated in step S31 to coincide with the target humidity. Specifically, based on the inlet temperature TI detected by the temperature sensor 26 and the outlet humidity HE, the controller 100 calculates absolute humidity. Likewise, based on the inlet temperature TI detected by the temperature sensor 26 and the target humidity, the controller 100 calculates target absolute humidity. If the calculated absolute humidity is lower than the target absolute humidity, the controller 100 changes the value of the third supply power W3 to a value larger than that in the current state. In contrast, if the calculated absolute humidity exceeds the target absolute humidity, the controller 100 changes the third supply power W3 to a value smaller than that in the current state. At this time, the greater a difference between the absolute humidity and the target absolute humidity, the more the controller 100 increases a variation in the third supply power W3 before and after the change. As described above, the controller 100 uses the inlet temperature TI detected by the temperature sensor 26 as a temperature condition. The controller 100 then performs, on the third supply power W3, feedback control based on the difference between the absolute humidity and the target absolute humidity, for example, PI control.

The target humidity described above is specified in advance by the user H or the medical worker such as a doctor and is stored in the memory 102 of the controller 100. Thereafter, the process by the controller 100 moves to step S33.

In step S33, the controller 100 executes a power supply process. Specifically, the controller 100 supplies each supply power calculated in step S21 to a corresponding one of the blower 20, the tube heater 92, and the heater 32 of the humidifier 30 for the fixed period of time. In the case where the process in step S33 is executed, the second supply power W2 is zero as described above. Accordingly, the first supply power W1 is supplied to the blower 20, and the third supply power W3 is supplied to the heater 32 of the humidifier 30. Thereafter, the process by the controller 100 again moves to step S31. That is, the controller 100 repeats steps S31 to S33.

If it is determined in step S12 described above that the tube heater 92 is properly attached (YES in step S12), the process by the controller 100 moves to step S13.

In step S13, the controller 100 estimates outlet temperature TE as the temperature of the air in the tube 91 and acquires the outlet temperature TE. Specifically, the controller 100 estimates the outlet temperature TE by adding an increase in temperature in the humidifier 30 and an increase in temperature caused by the tube heater 92 to the inlet temperature TI detected by the temperature sensor 26. The higher the water temperature TW detected by the water temperature sensor 33, the larger the increase in temperature in the humidifier 30. The larger the second supply power W2 to the tube heater 92, the larger the increase in temperature caused by the tube heater 92. In contrast, the higher the air flow rate F detected by the flow rate sensor 28, the smaller each of the increase in temperature in the humidifier 30 and the increase in temperature caused by the tube heater 92. Thereafter, the process by the controller 100 moves to step S14.

In step S14, the controller 100 estimates the outlet humidity HE and acquires the outlet humidity HE. The outlet humidity HE is estimated in the same manner as in step S31. Thereafter, the process by the controller 100 moves to step S15.

In step S15, the controller 100 executes the supply power calculation process. In step S15 as the supply power calculation process, the controller 100 calculates the first supply power W1 to the blower 20 to cause the air flow rate F detected by the flow rate sensor 28 to coincide with the target flow rate. The first supply power W1 is calculated in the same manner as in steps S21 and S32.

The controller 100 also calculates the second supply power W2 to the tube heater 92 to cause the outlet temperature TE estimated in step S13 to coincide with the target temperature. Specifically, if the outlet temperature TE is lower than the target temperature, the controller 100 makes the second supply power W2 higher than that in the current state. In contrast, if the outlet temperature TE exceeds the target temperature, the controller 100 makes the second supply power W2 lower than that in the current state. At this time, the greater a difference between the outlet temperature TE and the target temperature, the more the controller 100 increases a variation in the second supply power W2 before and after the change. As described above, the controller 100 performs, on the second supply power W2, feedback control based on the difference between the outlet temperature TE and the target temperature, for example, PI control. The target temperature described above is specified in advance by the user H or the medical worker such as a doctor and is stored in the memory 102 of the controller 100. In step S13, the outlet temperature TE is calculated based on the inlet temperature TI. In step S15, the second supply power W2 is calculated based on the outlet temperature TE. In this embodiment, the second supply power W2 is thus calculated based on the inlet temperature TI.

Further, the controller 100 calculates the third supply power W3 to the heater 32 of the humidifier 30 to cause the outlet humidity HE estimated in step S14 to coincide with the target humidity. Specifically, based on the outlet temperature TE estimated in step S13 and the outlet humidity HE estimated in step S14, the controller 100 calculates the absolute humidity. Likewise, based on the outlet temperature TE estimated in step S14 and the target humidity, the controller 100 calculates the target absolute humidity. If the calculated absolute humidity is lower than the target absolute humidity, the controller 100 changes the value of the third supply power W3 to a value larger than that in the current state. In contrast, if the calculated absolute humidity exceeds the target absolute humidity, the controller 100 changes the third supply power W3 to a value smaller than that in the current state. At this time, the greater the difference between the absolute humidity and the target absolute humidity, the more the controller 100 increases the variation in the third supply power W3 before and after the change. As described above, the controller 100 uses the outlet temperature TE estimated in step S13 as the temperature condition. The controller 100 then performs, on the third supply power W3, feedback control based on the difference between the absolute humidity and the target absolute humidity, for example, PI control. Thereafter, the process by the controller 100 moves to step S16.

In step S16, the controller 100 executes the power supply process. Specifically, the controller 100 respectively supplies the first supply power W1 and the second supply power W2 that are calculated in step S21 to the blower 20 and the tube heater 92 for the fixed period of time. In contrast, in a viewpoint of a level relationship, the controller 100 compares the third supply power W3 with remainder power obtained by subtracting the first supply power W1 and the second supply power W2 from a predetermined upper limit WL. The controller 100 supplies lower one of the remainder power described above and the third supply power W3 to the heater 32 of the humidifier 30 for the fixed period of time. That is, the controller 100 supplies the power preferentially to the blower 20 and the tube heater 92 and supplies the remainder power to the heater 32 of the humidifier 30. The upper limit WL is specified in advance and is stored in the memory 102 of the controller 100. The upper limit WL is defined as, for example, the rated output power of the AC/DC converter CV or a value slightly smaller than that of the rated output power. Thereafter, the process by the controller 100 moves to step S17.

In step S17, the controller 100 executes a determination process. The controller 100 thus determines whether a sum total WT of the first supply power W1, the second supply power W2, and the third supply power W3 that are calculated in step S15 is lower than or equal to the upper limit WL. If it is determined that the sum total WT is lower than or equal to the upper limit WL (YES in step S17), the process by the controller 100 again moves to step S13. The controller 100 then repeats steps S13 to S16. In contrast, if it is determined that the sum total WT exceeds the upper limit WL (NO in step S17), the process by the controller 100 moves to step S41.

Figure 6:
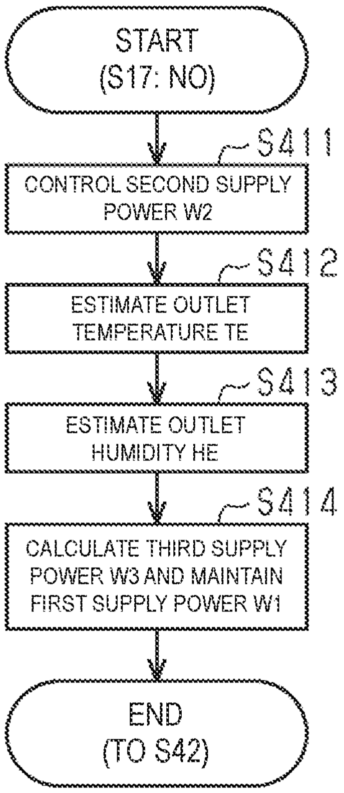
FIG. 6 is a flowchart of a changing process.

In step S41, the controller 100 executes a changing process. The changing process is a process in which the second supply power W2 is made lower than that in the current state. As illustrated in FIG. 6, the changing process is composed of steps S411 to S414.

Specifically, after staring the changing process, the controller 100 performs step S411. In step S411, the controller 100 controls the second supply power W2 in the current state and calculates new second supply power W2. Specifically, the controller 100 obtains a division value in such a manner that a value obtained by subtracting the inlet temperature TI detected by the temperature sensor 26 from the water temperature TW detected by the water temperature sensor 33 is divided by a value obtained by subtracting the inlet temperature TI detected by the temperature sensor 26 from the target temperature. The target temperature is normally considered to be set as temperature higher than the water temperature TW detected by the water temperature sensor 33. The division value described above is thus less than 1. The controller 100 then multiplies the second supply power W2 in the current state by the division value and obtains the new second supply power W2. Since the division value is less than 1 as described above, the second supply power W2 is decreased by performing step S411. Thereafter, the process by the controller 100 moves to step S412.

In step S412, the controller 100 estimates the outlet temperature TE and acquires the outlet temperature TE. The outlet temperature TE is estimated in step S412 in the same manner as for the estimation of the outlet temperature TE in step S13. However, the controller 100 estimates the outlet temperature TE in step S412 on the assumption that the new second supply power W2 calculated in step S411 is supplied to the tube heater 92. Note that the second supply power W2 calculated in step S411 is lower than the second supply power W2 before the recalculation. The outlet temperature TE estimated in step S412 thus has a value smaller than that of the outlet temperature TE estimated in step S13. Thereafter, the process by the controller 100 moves to step S413.

In step S413, the controller 100 estimates the outlet humidity HE and acquires the outlet humidity HE. The outlet humidity HE is estimated in step S413 in the same manner as for the estimation of the outlet humidity HE in step S14. Thereafter, the process by the controller 100 moves to step S414.

In step S414, the controller 100 maintains the value of the first supply power W1 calculated in step S15. In contrast, the controller 100 calculates the third supply power W3 to the heater 32 of the humidifier 30 to cause the outlet humidity HE estimated in step S413 to coincide with the target humidity. The third supply power W3 is calculated in step S414 in the same manner as in step S14. However, in step S414, the controller 100 calculates the absolute humidity and the target absolute humidity under the condition of the outlet temperature TE estimated in step S412. As the second supply power W2 in step S411 described above decreases, the value of the outlet temperature TE also becomes smaller. Although the outlet humidity HE is changed with the change of the outlet temperature TE, the absolute humidity is not changed in the calculation. In contrast, as the outlet temperature TE becomes lower, the target absolute humidity becomes lower. Accordingly, in step S414, the controller 100 calculates new third supply power W3 as a value slightly smaller than that of the third supply power W3 calculated in step S15. Thereafter, one cycle of the changing process is terminated, and the process by the controller 100 moves to step S42.

In step S42, the controller 100 executes the power supply process. Specifically, the controller 100 respectively supplies the first supply power W1 and the second supply power W2 that are calculated in step S21 to the blower 20 and the tube heater 92 for the fixed period of time. In contrast, in the viewpoint of a level relationship, the controller 100 compares the third supply power W3 with the remainder power obtained by subtracting the first supply power W1 and the second supply power W2 from the upper limit WL. The controller 100 then supplies lower one of the remainder power described above and the third supply power W3 changed in step S41 to the heater 32 of the humidifier 30 for the fixed period of time. Thereafter, the process by the controller 100 again moves to step S17. If the determination in step S17 has the negative result repeatedly, step S41 is repeated, and the second supply power W2 is gradually decreased as the result. That is, the changing process in step S41 is a process in which the second supply power W2 is gradually decreased until the sum total WT decreases to or below the upper limit WL.

Actions of this Embodiment

The CPAP device 10 includes the blower 20, the humidifier 30, and the tube heater 92 that are high power consumption devices. The upper limit WL of the power of the CPAP device 10 is basically set as a value that does not have trouble even if the blower 20, the humidifier 30, and the tube heater 92 are used simultaneously. However, it is possible that a drastic increase or the like of the first supply power W1 to be supplied to the blower 20 causes the sum total WT to temporarily exceed the upper limit WL.

Assume the following case. The CPAP device 10 is used in the docking state, and the sum total WT is lower than or equal to the upper limit WL. In addition, the outlet temperature TE coincides with the target temperature in this state, and the outlet humidity HE coincides with the target humidity. Further, an increase or the like in the first supply power W1 from the state as described above causes the sum total WT to temporarily exceed the upper limit WL.

In this case, in the embodiment above, immediately after the sum total WT exceeds the upper limit WL, the first supply power W1 is supplied to the blower 20. In addition, the second supply power W2 is supplied to the tube heater 92. The second supply power W2 at this time is a value yet to be controlled in the changing process. Accordingly, when the second supply power W2 is supplied to the tube heater 92, the outlet temperature TE still substantially coincides with the target temperature. In contrast, to the heater 32 of the humidifier 30, power only lower than the required third supply power W3 is supplied. However, the water stored in the water tank 31 of the humidifier 30 has a greater thermal capacity than air. Accordingly, the temperature of the water tank 31 does not decrease drastically.

Thereafter, if the state where the sum total WT exceeds the upper limit WL continues, the second supply power W2 decreases gradually. The decrease in the second supply power W2 causes an increase in the remainder power obtained by subtracting the first supply power W1 and the second supply power W2 from the upper limit WL. The power to be supplied to the humidifier 30 thus increases gradually. As the result, the temperature in the water tank 31 of the humidifier 30 is prevented from decreasing.

Effects of this Embodiment (1) With the CPAP device 10 of the embodiment above, immediately after the sum total WT exceeds the upper limit WL, the second supply power W2 or power close to the second supply power W2 is supplied to the tube heater 92. It is thus possible to maintain the outlet temperature TE close to the target temperature. Even if the humidified air flows through the tube 91, this maintainability of the outlet temperature TE close to the target temperature as described above enables the prevention of the water condensation in the tube 91. In contrast, even if the supply power to the humidifier 30 decreases, and if the decrease occurs immediately after the sum total WT exceeds the upper limit WL, the temperature of the water tank 31 does not decrease drastically, and thus the humidifier 30 keeps the humidifying performance. If the state where the sum total WT exceeds the upper limit WL continues, the power to be supplied to the humidifier 30 increases gradually. Accordingly, even though the state where the sum total WT exceeds the upper limit WL continues, the humidifier 30 keeps the heating function to some extent. As described above, with the CPAP device 10 of the embodiment above, it is less likely to impair the feel of the user H in following point. Even in the state where the sum total WT exceeds the upper limit WL, the water condensation is prevented, and the humidified air is also suppliable to the user H.

(2) In the CPAP device 10 of the embodiment above, the second supply power W2 is decreased in the changing process. The outlet temperature TE is then calculated on the assumption that the decreased second supply power W2 is supplied to the tube heater 92. Further, calculating the new third supply power W3 under this condition of the outlet temperature TE causes the third supply power W3 to be made lower than that before the recalculation. As described above, decreasing both of the second supply power W2 and the third supply power W3 in the changing process enables the sum total WT to enter a state lower than or equal to the upper limit at an early stage.

(3) In the CPAP device 10 of the embodiment above, even if the changing process is executed, the first supply power W1 is not changed. Accordingly, even if the changing process is executed, required power is supplied preferentially to the blower 20. Even in the state where the sum total WT exceeds the upper limit WL, it is thus less likely to influence the intrinsic therapy effects of the CPAP device 10.

(4) In the CPAP device 10 of the embodiment above, if the tube heater 92 is not properly attached, the second supply power W2 is calculated as zero, and the changing process is not executed. Accordingly, the third connector C3 is prevented from being energized unnecessarily. In addition, if the changing process for controlling the second supply power W2 is executed only in the case where the tube heater 92 is properly attached, the execution thereby enables processing load on the controller 100 to be reduced.

(5) In the CPAP device 10 of the embodiment above, if the first enclosure 11 is not attached to the second enclosure 12, the second supply power W2 and the third supply power W3 are calculated as zero, and the changing process is not executed. The first enclosure 11 not attached to the second enclosure 12 leads to the use of the CPAP device 10 without the humidifier 30. Accordingly, the tube heater 92 does not have to be used from the viewpoint of preventing the water condensation in the tube 91. That is, even if the second supply power W2 is zero, the second supply power W2 does not cause considerable trouble, and it is possible to prevent the first connector C1 to be energized unnecessarily. If the changing process for controlling the second supply power W2 is executed only in the case where the CPAP device 10 is in the docking state, the execution thereby enables the processing load on the controller 100 to be reduced.

Modifications

This embodiment may be implemented after modifications are made thereto as described below. This embodiment and the following modifications may be implemented in combination with each other without technical inconsistency.

In the embodiment above, any structure, for example, any shape of the main unit MU and the sub unit SU may be employed. The CPAP device 10 may also be composed of one unit integrally formed from the main unit MU and the sub unit SU. If the CPAP device 10 is composed of the one unit, steps S11, S21, and S22 in the power control are not required. Even if the CPAP device 10 is composed of the two units as in the embodiment above, steps S11, S21, and S22 in the power control may be omitted.

The CPAP device 10 may further include another unit in addition to the main unit MU and the sub unit SU.

The tube 91 and the tube heater 92 do not have to be attachable to and detachable from the sub unit SU. The tube 91 and the tube heater 92 may thus be fixed onto the sub unit SU. In this case, step S12 and steps S31 to S33 in the power control are not required. Even if the tube heater 92 is attachable to and detachable from the sub unit SU as in the embodiment above, step S12 and steps S31 to S33 in the power control may be omitted.

The silencer 40 of the sub unit SU may be located downstream of the blower 20. The silencer 40 may also be omitted. Further, instead of or in addition to the silencer 40 of the sub unit SU, the main unit MU may have a silencer.

The sub unit SU or the main unit MU does not have to have the silencer. Instead of or in addition to the silencer of any of these units, for example, the silencer may be provided along the course of the tube 91 or between the tube 91 and the mask 93.

The main unit MU may be provided with a rechargeable battery. If the CPAP device 10 has a built-in battery, the power outputted from the battery is likely to be low. The CPAP device 10 having the built-in battery is thus an example preferable to apply the power control described above.

The configuration of the humidifier 30 may be modified. Any humidifier 30 capable of humidifying air and operating in response to receiving power supply may be subjected to the power control in the embodiment above. For example, the humidifier 30 may be an ultrasonic humidifier.

Instead of the water temperature sensor 33, a sensor that detects the temperature of the heater 32 or the heater plate may be provided. In this case, a detection value of the sensor that detects the temperature of the heater 32 or the heater plate may be handled as the water temperature TW.

Any configuration of the operation part 25 may be employed. A different input device may be configured to be connected in addition to or instead of the operation part 25. In this case, communication between the CPAP device 10 and the input device may be performed by using a wired or wireless communication system.

The configuration of the controller 100 may be changed appropriately. The controller 100 may thus be configured as circuitry including one or more processors that execute various processes in accordance with a computer program (software), one or more dedicated hardware circuits, such as an application specific integrated circuit (ASIC), that execute at least part of the various processes, or the combination thereof. The processor includes a central processing unit (CPU) and a memory such as a RAM or a ROM, and the memory stores program code or instructions configured to cause the CPU to execute a process. The memory, that is, a computer readable medium includes any usable medium accessible by a general-purpose or dedicated computer.

The temperature sensor 26 is not limited to the sensor that detects the temperature of the air in the upstream passage 61 and may be a sensor that detects, for example, the temperature of the downstream passage 62. The upstream passage 61 or the downstream passage 62 may be provided with a plurality of temperature sensors 26, and thereby the mean value or the like of the temperature sensors 26 may be used as the inlet temperature TI. In this point, the same holds true for the humidity sensor 27 and the flow rate sensor 28.

The temperature sensor 26 may be omitted. If the temperature sensor 26 is omitted, the controller 100 may handle the inlet temperature TI as a fixed value, for example, 27° C.

The humidity sensor 27 may be omitted. If the humidity sensor 27 is omitted, the controller 100 may handle the inlet humidity HI as a fixed value, for example, 50%.

The flow rate sensor 28 may be omitted. If the flow rate sensor 28 is omitted, the air flow rate F may be estimated from the number of revolutions or the like of the electric motor of the blower 20.

In the power control, the specific method for estimating the outlet temperature TE may be changed appropriately. Instead of estimating the outlet temperature TE, the outlet temperature TE may be actually measured. In this case, a temperature sensor may be attached to the fourth passage 54 of the sub unit SU or the tube 91.

In the power control, the specific method for estimating the outlet humidity HE may be changed appropriately. Instead of estimating the outlet humidity HE, the outlet humidity HE may be actually measured. In this case, a humidity sensor may be attached to the fourth passage 54 of the sub unit SU or the tube 91.

It is not essential to set the target temperature of the outlet temperature TE. For example, the memory 102 may store any of a map and an arithmetic expression that store the relationship between the inlet temperature TI and the second supply power W2. In this case, a preferable relationship is that the lower the inlet temperature TI, the higher the second supply power W2. Even if the memory 102 does not have data as the target temperature, the relationship as described above leads to the outlet temperature TE closer to the target temperature assumed as preferable temperature in designing.

The specific method for calculating the first supply power W1, the second supply power W2, and the third supply power W3 in step S15 in the power control may be changed appropriately. These supply powers may be calculated in feedback control other than the PI control. For example, the supply power may be calculated in proportional (P) control or proportional integral derivative (PID) control. Further, the second supply power W2 and the third supply power W3 may be specified in advance, not in the feedback control. For example, the multiple heating levels such as high, medium, and low may be specified in advance for the tube heater 92 and may be configured to enable the user H to select one of these. The second supply power W2 may be specified in advance for each of the levels of high, medium, and low. In this point, the same holds true for the supply power calculation in the steps other than step S15. The calculation is not limited to calculation using an arithmetic expression or the like. As in this modification, the term "supply power calculation" applies to even the case where the second supply power W2 and the third supply power W3 are read out as predetermined values from the memory 102.

In the changing process, the method for decreasing the second supply power W2 is not limited to the example in the embodiment above. For example, the new second supply power W2 may be calculated by subtracting a predetermined fixed value from the second supply power W2 before the control.

In the changing process, the second supply power W2 may be decreased based on a difference between the sum total WT and the upper limit WL. In this case, for example, it suffices that the memory 102 stores any of a map and an arithmetic expression that store a relationship between the difference obtained by subtracting the upper limit WL from the sum total WT and the difference in the decrease in the second supply power W2. It is preferable in the relationship described above that the greater the difference obtained by subtracting the upper limit WL from the sum total WT, the greater the difference in the decrease in the second supply power W2. According to this modification, the new second supply power W2 may be calculated by a simple arithmetic operation, and repeating the changing process causes the second supply power W2 to decrease until the sum total WT becomes lower than or equal to the upper limit WL.

In the modification above, the difference in the decrease in the second supply power W2 may also be set greater than the difference obtained by subtracting the upper limit WL from the sum total WT. In this case, it is preferable that in the changing process, the third supply power W3 is calculated as a value obtained by subtracting the first supply power W1 and the decreased second supply power W2 from the upper limit WL. Calculating in this manner causes the sum total WT to become lower than or equal to the upper limit WL in one time changing process.

Further, in the modification above, in response to the decrease in the second supply power W2, the third supply power W3 may be increased. In this case, an increase in the third supply power W3 is required to be smaller than the decrease in the second supply power W2. Specifically, the sum of the second supply power W2 and the third supply power W3 after the changing process is required to be smaller than the sum before the changing process.

In the changing process, the third supply power W3 may be decreased based on the difference between the sum total WT and the upper limit WL. In this modification, a decrease in the third supply power W3 is preferably greater than the difference between the sum total WT and the upper limit WL. In this case, in the changing process, the second supply power W2 is preferably calculated as a value obtained by subtracting the first supply power W1 and the decreased third supply power W3 from the upper limit WL. The second supply power W2 is required to be decreased after the changing process as compared with that before the changing process.

In the changing process, the third supply power W3 calculated in step S15 may be maintained without calculating the new third supply power W3.

In the changing process, the first supply power W1 may be changed. For example, new first supply power W1 may be calculated by subtracting a predetermined fixed value from the first supply power W1 before the control. However, it is preferable to specify a lower limit of the first supply power W1 in advance to exert therapy effects by the CPAP device 10 and then change the first supply power W1 within a range of the lower limit or higher.

APPENDIXES

The following describe technical ideas derivable from the embodiment and the modifications above.

Appendix 1

A CPAP device includes: a blower that blows air; a tube that allows air blown by the blower to flow through the tube; a tube heater that heats the air in the tube; a humidifier that humidifies the air blown into the tube; and a controller that controls power supply to the blower, the humidifier, and the tube heater. The controller is configured to execute a supply power calculation process in which each of first supply power to the blower, second supply power to the tube heater, and third supply power to the humidifier is calculated, a determination process in which whether a sum total of the first supply power, the second supply power, and the third supply power exceeds a predetermined upper limit is determined, a power supply process in which the first supply power is supplied to the blower, the second supply power is supplied to the tube heater, and lower one of remainder power and the third supply power is supplied to the humidifier, the remainder power being obtained by subtracting the first supply power and the second supply power from the upper limit, and a changing process in which in response to the sum total exceeding the upper limit, the second supply power is decreased until the sum total decreases to or below the upper limit.

Appendix 2

In the CPAP device according to Appendix 1, the controller, in the supply power calculation process, calculates the second supply power based on inlet temperature of the air to be blown into the tube and calculates the third supply power to cause outlet humidity of the air in the tube to be closer to target humidity, and in the changing process, acquires outlet temperature of the air in the tube, the outlet temperature being estimated on assumption that the decreased second supply power is supplied to the tube heater, and calculates the third supply power to cause the outlet humidity under a condition of the outlet temperature to coincide with the target humidity.

Appendix 3

In the CPAP device according to Appendix 1, the controller decreases the second supply power in the changing process, the second supply power being decreased based on a difference between the sum total and the upper limit.

Appendix 4

In the CPAP device according to any one of Appendixes 1 to 3, in the changing process, the controller does not change a value of the first supply power, the value being calculated in the supply power calculation process.

Appendix 5

The CPAP device according to any one of Appendixes 1 to 4 further includes: an enclosure that accommodates the controller and the blower. In the CPAP device, the tube heater is attachable to and detachable from the enclosure, and in absence of attachment of the tube heater to the enclosure, the controller calculates the second supply power as zero in the supply power calculation process and does not execute the changing process.

Appendix 6

The CPAP device according to any one of Appendixes 1 to 5 further includes: a first enclosure that accommodates the controller and the blower; and a second enclosure that accommodates the humidifier and to and from which the first enclosure is attachable and detachable. In the CPAP device, the tube is attachable to and detachable from each of the first enclosure and the second enclosure, and in absence of attachment of the first enclosure to the second enclosure, the controller calculates the second supply power and the third supply power as zero in the supply power calculation process and does not execute the changing process.

Appendix 7

A power control program for a CPAP device is provided, the CPAP device including a blower that blows air, a tube that allows air blown by the blower to flow through the tube, a tube heater that heats the air in the tube, a humidifier that humidifies the air blown into the tube, and a controller that controls power supply to the blower, the humidifier, and the tube heater. The program causes the controller to execute a supply power calculation process in which each of first supply power to the blower, second supply power to the tube heater, and third supply power to the humidifier is calculated, a determination process in which whether a sum total of the first supply power, the second supply power, and the third supply power exceeds a predetermined upper limit is determined, a power supply process in which the first supply power is supplied to the blower, the second supply power is supplied to the tube heater, and lower one of remainder power and the third supply power is supplied to the humidifier, the remainder power being obtained by subtracting the first supply power and the second supply power from the upper limit, and a changing process in which in response to the sum total exceeding the upper limit, the second supply power is decreased until the sum total decreases to or below the upper limit.

What is claimed is:

1. A continuous positive airway pressure (CPAP) device comprising:

a blower configured to blow air;

a tube through which air blown by the blower flows through;

a tube heater configured to heat the air in the tube;

a humidifier configured to humidify the air blown into the tube; and a controller configured to control power supply to the blower, the humidifier, and the tube heater, wherein the controller is configured to:

determine a first supply power to the blower, a second supply power to the tube heater, and a third supply power to the humidifier, determine whether a sum total of the first supply power, the second supply power, and the third supply power exceeds an upper limit, control supply of the first supply power to the blower, the second supply power to the tube heater, and a lesser of a remainder power and the third supply power to the humidifier, the remainder power being a difference of the first supply power and the second supply power from the upper limit, in response to the sum total exceeding the upper limit, decrease the second supply power until the sum total decreases to or below the upper limit, determine the second supply power based on an inlet temperature of the air blown into the tube, determine the third supply power such that an outlet humidity of the air in the tube approaches a target humidity, acquire an outlet temperature of the air in the tube, the outlet temperature being estimated on assumption that the decreased second supply power is supplied to the tube heater, and determine the third supply power such that the outlet humidity under a condition of the outlet temperature coincides with the target humidity.

2. The CPAP device according to claim 1, wherein the controller is configured to decrease the second supply power based on a difference between the sum total and the upper limit.

3. The CPAP device according to claim 1, wherein the controller is configured to not change the first supply power.

4. The CPAP device according to claim 1, further comprising:

an enclosure that accommodates the controller and the blower, wherein the tube heater is attachable to and detachable from the enclosure, and wherein in absence of attachment of the tube heater to the enclosure, the controller is configured to determine the second supply power as zero and to not change the second supply power.

5. The CPAP device according to claim 1, further comprising:

a first enclosure that accommodates the controller and the blower; and a second enclosure that accommodates the humidifier, and to and from which the first enclosure is attachable and detachable, wherein the tube is attachable to and detachable from each of the first enclosure and the second enclosure, and wherein in absence of attachment of the first enclosure to the second enclosure, the controller is configured to determine the second supply power and the third supply power as zero and to not change the second supply power.

6. A non-transitory computer-readable medium having instructions stored thereon for execution by a (CPAP) device comprising a blower configured to blow air, a tube through which air blown by the blower flows through, a tube heater configured to heat the air in the tube, a humidifier configured to humidify the air blown into the tube, and a controller configured to control power supply to the blower, the humidifier, and the tube heater, the controller being configured to, when executing the instructions, cause the CPAP device to:

determine a first supply power to the blower, a second supply power to the tube heater, and a third supply power to the humidifier, determine whether a sum total of the first supply power, the second supply power, and the third supply power exceeds a predetermined upper limit, control supply of the first supply power to the blower, the second supply power to the tube heater, and a lesser one of a remainder power and the third supply power to the humidifier, the remainder power being a difference of the first supply power and the second supply power from the upper limit, in response to the sum total exceeding the upper limit, decrease the second supply power until the sum total decreases to or below the upper limit, determine the second supply power based on an inlet temperature of the air blown into the tube, determine the third supply power such that an outlet humidity of the air in the tube approaches a target humidity, acquire an outlet temperature of the air in the tube, the outlet temperature being estimated on assumption that the decreased second supply power is supplied to the tube heater, and determine the third supply power such that the outlet humidity under a condition of the outlet temperature coincides with the target humidity.

* * * * *